(12) United States Patent
Hattersley et al.

(10) Patent No.: US 9,234,877 B2
(45) Date of Patent: Jan. 12, 2016

(54) MAGNETIC DETECTOR

(71) Applicants: Endomagnetics Ltd., Cambridge (GB); University of Houston, Houston, TX (US)

(72) Inventors: Simon Richard Hattersley, Kent (GB); Peter Georg Laitenberger, Cambridge (GB); Audrius Brazdeikis, Missouri City, TX (US)

(73) Assignees: Endomagnetics LTD., Cambridge (GB); University of Houston, Houston, TX (US)

( * ) Notice: Subject to any disclaimer, the term of this patent is extended or adjusted under 35 U.S.C. 154(b) by 253 days.

(21) Appl. No.: 13/799,334

(22) Filed: Mar. 13, 2013

(65) Prior Publication Data

US 2014/0266174 A1    Sep. 18, 2014

(51) Int. Cl.
| | |
|---|---|
| *G01R 33/12* | (2006.01) |
| *G01R 33/28* | (2006.01) |
| *A61B 5/05* | (2006.01) |
| *G01N 27/74* | (2006.01) |
| *G01R 33/02* | (2006.01) |
| *G01R 33/10* | (2006.01) |

(52) U.S. Cl.
CPC ............ *G01N 27/745* (2013.01); *A61B 5/05* (2013.01); *G01R 33/0213* (2013.01); *G01R 33/10* (2013.01)

(58) Field of Classification Search
CPC ...... G01R 33/12; G01R 33/02; G01R 33/035; G01R 33/285; G01N 27/72; G01N 33/54326; G01N 33/54346; A61B 5/05; A61B 17/34; A61B 5/055; A61B 5/06; A61B 5/0515; A61B 19/54; A61B 6/12

USPC ........ 324/232, 243–244; 600/10, 12, 17, 310, 600/409, 411, 417, 424, 420, 443
See application file for complete search history.

(56) References Cited

U.S. PATENT DOCUMENTS

| | | |
|---|---|---|
| 2,614,164 A | 10/1952 | Huston |
| 3,445,928 A | 5/1969 | Beynon |

(Continued)

FOREIGN PATENT DOCUMENTS

| | | |
|---|---|---|
| DE | 29724862 | 2/2005 |
| DE | 29724862 | 3/2005 |

(Continued)

OTHER PUBLICATIONS

Harnan, S.E. et al.; "Magnetic resonance for assessment of axillary lymph node status in early breast cancer: A systematic review and meta-analysis"; EJSO The Journal of Cancer Surgery; 2011; vol. 37, pp. 928-936.

(Continued)

*Primary Examiner* — Tung X Nguyen
*Assistant Examiner* — Neel Shah
(74) *Attorney, Agent, or Firm* — K&L Gates LLP

(57) ABSTRACT

A probe for detecting magnetic particles. In one embodiment, the probe includes: a cylindrical probe core having a first end and a second end, the cylindrical probe core defining two channels for containing coils of wire, one of the channels being adjacent the first end of the cylindrical probe core; two sense coils, one each of the sense coils being located in a respective one of the channels; and two drive coils, one each of the drive coils being co-located with the respective sense coil in a respective one of the channels.

18 Claims, 5 Drawing Sheets

(56) References Cited

U.S. PATENT DOCUMENTS

| | | | |
|---|---|---|---|
| 3,449,662 A | 6/1969 | Wood | |
| 4,324,255 A | 4/1982 | Barach et al. | |
| 4,825,162 A | 4/1989 | Roemer et al. | |
| 4,983,912 A | 1/1991 | Roehrlein et al. | |
| 5,005,001 A | 4/1991 | Cordery | |
| 5,184,070 A | 2/1993 | Besendorfer et al. | |
| 5,261,403 A | 11/1993 | Saito et al. | |
| 5,293,119 A | 3/1994 | Podney | |
| 5,363,845 A | 11/1994 | Chowdhury et al. | |
| 5,402,094 A | 3/1995 | Enge | |
| 5,414,356 A | 5/1995 | Yoshimura et al. | |
| 5,416,413 A | 5/1995 | Leussler | |
| 5,437,280 A | 8/1995 | Hussman | |
| 5,512,821 A | 4/1996 | Ando et al. | |
| 5,534,778 A | 7/1996 | Loos et al. | |
| 5,537,037 A | 7/1996 | Otaka et al. | |
| 5,657,756 A | 8/1997 | Vrba et al. | |
| 5,666,052 A | 9/1997 | Sata | |
| 5,844,140 A | 12/1998 | Seale | |
| 5,942,209 A | 8/1999 | Leavitt et al. | |
| 5,997,473 A | 12/1999 | Taniguchi et al. | |
| 6,076,008 A | 6/2000 | Bucholz | |
| 6,082,366 A | 7/2000 | Andra et al. | |
| 6,173,715 B1 | 1/2001 | Sinanan et al. | |
| 6,205,352 B1 | 3/2001 | Carroll | |
| 6,230,038 B1 | 5/2001 | von Gutfeld et al. | |
| 6,270,464 B1 | 8/2001 | Fulton, III et al. | |
| 6,304,075 B1 | 10/2001 | von Schaewen et al. | |
| 6,347,241 B2 | 2/2002 | Burbank et al. | |
| 6,356,782 B1 | 3/2002 | Sirimanne et al. | |
| 6,371,904 B1 | 4/2002 | Sirimanne et al. | |
| 6,394,965 B1 | 5/2002 | Klein | |
| 6,406,420 B1 | 6/2002 | McCarthy et al. | |
| 6,418,335 B2 | 7/2002 | Avrin et al. | |
| 6,427,081 B1 | 7/2002 | Burbank et al. | |
| 6,445,185 B1 | 9/2002 | Damadian et al. | |
| 6,549,800 B1 | 4/2003 | Atalar et al. | |
| 6,592,608 B2 | 7/2003 | Fisher et al. | |
| 6,603,308 B2 | 8/2003 | Itozaki et al. | |
| 6,638,913 B1 | 10/2003 | Speck et al. | |
| 6,662,040 B1 | 12/2003 | Henrichs et al. | |
| 6,662,041 B2 | 12/2003 | Burbank et al. | |
| 6,699,205 B2 | 3/2004 | Fulton, III et al. | |
| 6,725,083 B1 | 4/2004 | Burbank et al. | |
| 6,766,186 B1 | 7/2004 | Hoyns et al. | |
| 6,815,949 B2 | 11/2004 | Kandori et al. | |
| 6,835,572 B1 | 12/2004 | Mountford et al. | |
| 6,850,065 B1 | 2/2005 | Fujita et al. | |
| 6,862,470 B2 | 3/2005 | Burbank et al. | |
| 6,889,073 B2 | 5/2005 | Lampman et al. | |
| 6,920,346 B2 | 7/2005 | Kazandjian et al. | |
| 6,949,926 B2 | 9/2005 | Murakami et al. | |
| 6,963,769 B1 | 11/2005 | Balaban et al. | |
| 6,996,433 B2 | 2/2006 | Burbank et al. | |
| 7,009,398 B2 | 3/2006 | Hahn et al. | |
| 7,044,957 B2 | 5/2006 | Foerster et al. | |
| 7,084,631 B2 | 8/2006 | Qu et al. | |
| 7,116,094 B2 | 10/2006 | Levin et al. | |
| 7,229,417 B2 | 6/2007 | Foerster et al. | |
| 7,283,868 B2 | 10/2007 | Ko et al. | |
| 7,329,414 B2 | 2/2008 | Fisher et al. | |
| 7,335,511 B2 | 2/2008 | Mountford et al. | |
| 7,386,338 B2 | 6/2008 | Hoppel et al. | |
| 7,412,275 B2 | 8/2008 | Marinelli | |
| 7,416,533 B2 | 8/2008 | Gellman et al. | |
| 7,479,784 B2 | 1/2009 | Lee | |
| 7,525,308 B2 | 4/2009 | Tsukada et al. | |
| 7,535,363 B2 | 5/2009 | Gisselberg et al. | |
| 7,570,056 B2 | 8/2009 | Nakabayashi et al. | |
| 7,625,397 B2 | 12/2009 | Foerster et al. | |
| 7,668,582 B2 | 2/2010 | Sirimanne et al. | |
| 7,676,256 B2 | 3/2010 | Satragno et al. | |
| 7,680,524 B2 | 3/2010 | Ogawa et al. | |
| 7,689,267 B2 | 3/2010 | Prince | |
| 7,701,209 B1 | 4/2010 | Green | |
| 7,702,378 B2 | 4/2010 | Bolan et al. | |
| 7,711,407 B2 | 5/2010 | Hughes et al. | |
| 7,744,852 B2 | 6/2010 | Chernomorsky et al. | |
| 7,783,336 B2 | 8/2010 | Macfarlane et al. | |
| 7,792,569 B2 | 9/2010 | Burbank et al. | |
| 7,877,133 B2 | 1/2011 | Burbank et al. | |
| 7,972,619 B2 | 7/2011 | Fisher | |
| 8,050,742 B2 | 11/2011 | Weizman | |
| 8,060,183 B2 | 11/2011 | Leopold et al. | |
| 8,062,215 B2 | 11/2011 | Voegele et al. | |
| 8,064,987 B2 | 11/2011 | Carr, Jr. | |
| 8,118,754 B1 | 2/2012 | Flynn et al. | |
| 8,137,320 B2 | 3/2012 | Mark et al. | |
| 8,174,259 B2 | 5/2012 | Hattersley et al. | |
| 8,219,182 B2 | 7/2012 | Burbank et al. | |
| 8,277,391 B2 | 10/2012 | Foerster et al. | |
| 8,280,486 B2 | 10/2012 | Miller et al. | |
| 2001/0011155 A1 | 8/2001 | Rapoport | |
| 2001/0012915 A1 | 8/2001 | Avrin et al. | |
| 2001/0049481 A1 | 12/2001 | Fulton, III et al. | |
| 2002/0019595 A1 | 2/2002 | Osborne et al. | |
| 2002/0035324 A1 | 3/2002 | Sirimanne et al. | |
| 2002/0161298 A1 | 10/2002 | Burbank et al. | |
| 2003/0016010 A1 | 1/2003 | Kandori et al. | |
| 2003/0078493 A1 | 4/2003 | Ogawa et al. | |
| 2003/0141868 A1 | 7/2003 | Bakharev | |
| 2003/0214313 A1 | 11/2003 | Omura et al. | |
| 2003/0216632 A1 | 11/2003 | McClure et al. | |
| 2004/0052034 A1* | 3/2004 | Senba et al. | 361/600 |
| 2004/0109823 A1 | 6/2004 | Kaplan | |
| 2004/0138555 A1* | 7/2004 | Krag et al. | 600/424 |
| 2004/0162477 A1 | 8/2004 | Okamura et al. | |
| 2004/0236213 A1 | 11/2004 | Jones et al. | |
| 2004/0249261 A1 | 12/2004 | Torchia et al. | |
| 2005/0033157 A1 | 2/2005 | Klein et al. | |
| 2005/0059881 A1 | 3/2005 | Balaban et al. | |
| 2005/0148863 A1 | 7/2005 | Okamura et al. | |
| 2006/0074295 A1 | 4/2006 | Kucharczyk et al. | |
| 2006/0173283 A1 | 8/2006 | Axelsson et al. | |
| 2006/0258933 A1 | 11/2006 | Ellis et al. | |
| 2006/0270930 A1 | 11/2006 | Brasile | |
| 2006/0293581 A1 | 12/2006 | Plewes et al. | |
| 2007/0093726 A1 | 4/2007 | Leopold et al. | |
| 2008/0074109 A1 | 3/2008 | Tsukada et al. | |
| 2008/0097199 A1 | 4/2008 | Mullen | |
| 2008/0146914 A1 | 6/2008 | Polzin et al. | |
| 2008/0161848 A1 | 7/2008 | Fisher | |
| 2008/0214930 A1 | 9/2008 | Brasile | |
| 2008/0228164 A1 | 9/2008 | Nicoson et al. | |
| 2008/0275333 A1 | 11/2008 | Fain et al. | |
| 2008/0294036 A1 | 11/2008 | Hoi et al. | |
| 2009/0024022 A1 | 1/2009 | Azar et al. | |
| 2009/0082662 A1 | 3/2009 | Israel | |
| 2009/0118611 A1 | 5/2009 | He | |
| 2009/0164161 A1 | 6/2009 | Hong et al. | |
| 2009/0201016 A1* | 8/2009 | Hattersley et al. | 324/239 |
| 2009/0216113 A1* | 8/2009 | Meier et al. | 600/424 |
| 2010/0030149 A1 | 2/2010 | Carr, Jr. | |
| 2010/0099978 A1 | 4/2010 | Geppert et al. | |
| 2010/0125191 A1 | 5/2010 | Sahin | |
| 2010/0305430 A1 | 12/2010 | Troesken | |
| 2011/0021888 A1 | 1/2011 | Sing et al. | |
| 2011/0133730 A1* | 6/2011 | Hattersley | 324/239 |
| 2011/0137154 A1 | 6/2011 | Hattersley et al. | |
| 2012/0229130 A1 | 9/2012 | Hattersley et al. | |

FOREIGN PATENT DOCUMENTS

| | | |
|---|---|---|
| DE | 102007009016 | 8/2008 |
| EP | 0126580 | 11/1984 |
| EP | 0595227 | 5/1994 |
| EP | 0663599 | 5/1997 |
| EP | 1249207 | 10/2002 |
| EP | 0966924 | 8/2003 |
| EP | 1284123 | 7/2005 |
| EP | 1062911 | 6/2007 |
| EP | 1491147 | 3/2010 |
| EP | 2267471 | 12/2010 |
| EP | 2339343 A1 | 6/2011 |

(56) References Cited

FOREIGN PATENT DOCUMENTS

| | | |
|---|---|---|
| FR | 2689638 | 4/1992 |
| FR | 2770779 | 5/1999 |
| GB | 2109112 | 5/1983 |
| GB | 2425610 | 1/2006 |
| JP | 02-078983 | 3/1990 |
| JP | 02-281170 | 11/1990 |
| JP | 05-251774 | 9/1993 |
| JP | 06-324021 | 11/1994 |
| JP | 08-015229 | 1/1996 |
| JP | 08-248004 | 9/1996 |
| JP | 08-338864 | 12/1996 |
| JP | 09-027057 | 1/1997 |
| JP | 10-038854 | 2/1998 |
| JP | 2003-149212 | 5/2003 |
| JP | 2005-168678 | 6/2005 |
| JP | 2006-030004 | 2/2006 |
| WO | 9504287 | 2/1995 |
| WO | 9807052 | 2/1998 |
| WO | 0038579 | 7/2000 |
| WO | 02/39917 A1 | 5/2002 |
| WO | 0239917 | 5/2002 |
| WO | 2005011512 | 2/2005 |
| WO | 2006009048 | 1/2006 |
| WO | 2006022786 | 3/2006 |
| WO | 2006056739 | 6/2006 |
| WO | 2006117530 | 11/2006 |
| WO | 2007034196 | 3/2007 |
| WO | 2007053533 | 5/2007 |
| WO | 2011033306 | 3/2011 |
| WO | 2011067576 | 6/2011 |
| WO | 2014/013235 A1 | 1/2014 |

OTHER PUBLICATIONS

Material Safety Data Sheet; Revision Date Mar. 5, 2007; Retrieved from the internet: URL:https://tools.lifetechnologies.com/content/sfs/msds/2007/11361DVIAL1:MTR-NAIV_EN.pdf [retrieved on Jun. 10, 2014]; abstract; (6 pages).

Tsay, Tzong T. et al.; "Deep Cervical Lymph Flow Following the Infusion of Mannitol in Rabbits"; Life Sciences; 1997; vol. 61, No. 19; pp. 1929-1934.

Cash, et al., "Breast Cancers: Noninvasive Method of Preoperative Localization with Three-dimensional US and Surface Contour Mapping," Published online before print Sep. 21, 2007, doi: 10.1148/radiol.2452060906; Nov. 2007 Radiology, 245, pp. 556-566 (downloaded on Sep. 28, 2011 from http://radiology.rsna.org/content/245/2/556.full).

Conners, "Diagnostic uses of metal detectors: a review," Int. J. Clin. Pract. Aug. 2005:59(8), pp. 946-949, Blackwell Publishing Ltd.

Fagaly, "Squid Detection of Electronic Circuits," IEEE Transactions on Magnetics, vol. 25, No. 2, Mar. 1989, pp. 1216-1218.

Freitas Jr., "Nanomedicine, vol. I: Basic Capabilities," www.nanomedicine.com/NMI/8.2.1.2.htm, Landes Bioscience, Georgetown, TX, 1999, 4 pages.

Gopee, et al., "Migration of Intradermally Injected Quantum Dots to Sentinel Organs in Mice," Toxicological Sciences, vol. 98(1), Apr. 2007, pp. 249-257.

Gunasekera, et al., "Imaging applications of nanotechnology in cancer," Targeted Oncology, 2009, vol. 4, pp. 169-181.

Jakub, et al., "Current Status of radioactive seed for localization of non palpable breast lesions," The American Journal of Surgery, Apr. 2010, vol. 199, No. 4, pp. 522-528.

Kim, et al., "Near-infrared fluorescent type II quantum dots for sentinel lymph node mapping," Nat Biotechnol., vol. 22 (1), Jan. 2004, pp. 93-97.

Meenach, "Synthesis and Characterixation of Magnetic Hydrogel Nanocomposites for Cancer Therapy Applications," University of Kentucky Doctoral Dissertations, 2010, paper 108, http://uknowledge.uky.edu/gradschool_diss/108.

Noguchi, et al., "Sentinel lymphadenectomy in breast cancer: identification of sentinel lymph node and detection of metastases," Breast Cancer Research and Treatment, vol. 53, 1999, pp. 97-104.

Peleg, et al., "Implementing metal detector technology and a navigation system in the removal of shrapnel," Computer Aided Surgery, Dec. 2009, vol. 14, No. 1-3; pp. 63-68.

Peleg, et al., "Integration of computer-aided navigation and metal detector technology in the removal of shrapnel in terror attacks casualties," 7th Int. Conf. Computer-Aided Orthopaedic Surgery, Heidelberg, Germany, 2007, pp. 57-60.

Postma, et al., "Localization of nonpalpable breast lesions," Expert Rev. Anticancer Ther. vol. 11, No. 8, 2011, pp. 1295-1302.

Reddy, et al., "Preparation & application of magnetic hydrogel nanocomposites for pritein purification and metal absorption," International Conference on Advances in Polymer Technology, Feb. 26-27, 2010, India, pp. 83-97.

Soltesz, et al., "Intraoperative Sentinel Lymph Node Mapping of the Lung Using Near-Infrared Fluorescent Quantum Dots," Ann Thorac. Surg., vol. 79(1), Jan. 2005, pp. 269-277 (reproduced from NIH Public Access).

PCT International Search Report and Written Opinion of International Searching Authority for International Patent Application No. PCT/GB2010/002233, mailed Mar. 16, 2011, 15 pages.

PCT International Search Report and Written Opinion of International Searching Authority for International Patent Application No. PCT/GB2013/051885, mailed Nov. 14, 2013, 18 pages.

English translation of Official Action for Japanese Patent Application No. 2008-508306, dispatched on Nov. 8, 2011, 6 pages.

European Search Report for EP 10180206, Nov. 23, 2010, 4 pages.

Williamson, S.J. et al.; "Biomagnetism"; Journal of Magnetism and Magnetic Materials; XP000574230; 1981; vol. 22; pp. 129-201.

* cited by examiner

MAGNETIC DETECTOR

RELATED APPLICATIONS

This application is related to the U.S. patent application Ser. No. 13/799,480, being filed concurrently herewith, the contents of which are incorporated by reference in their entirety.

FIELD OF THE INVENTION

The invention relates generally to the field of medical devices for locating tissue in preparation for surgery and more specifically for detecting magnetic markers in tissue for excision.

BACKGROUND

The recent use of magnetic sensor probes to detect magnetic nanoparticles in the localization of sentinel lymph nodes in the staging of cancer in preparation for surgery has made the job of determining the location of the sentinel nodes easier for the surgeon. Further, the use of a probe to detect magnetic markers has also made relocating biopsy sites easier after pathology microscopic examination of excised tissue.

The inventors of the sensor probes for these systems seek to improve the design by: reducing thermal effects which cause coils in the sensor to shift with respect to one another and reduce the ability of the user to detect the signal from the magnetic nanoparticles; reducing interference caused by diamagnetic responses due to the body itself; and reducing the interference caused by eddy currents induced in objects near the sensor probe. In addition, it is desired that all these functional improvements be accomplished using a smaller sized probe with heightened sensitivity.

The present invention addresses this need.

SUMMARY OF THE INVENTION

In one aspect, the invention relates to a probe for detecting a magnetic marker. In one embodiment, the probe includes a probe core having a first end and a second end, the probe core defining two regions for containing coils of wire, one of the regions being adjacent the first end of the cylindrical probe core; two sense coils, one each of the sense coils being located in a respective one of the regions; and two drive coils, one each of the drive coils being located in a respective one of the regions, wherein the regions are separated by a distance equal to or greater than the diameter of one of the coils. In another embodiment, the magnetic marker comprises magnetic nanoparticles. In yet another embodiment, one of the set of two drive coils and the set of two sense coils is connected as a gradiometer, and the other of the set of two drive coils and the set of two sense coils is connected in series. In still yet another embodiment, the regions of the probe core define two channels for containing coils of wire, one of the channels being adjacent the first end of the cylindrical probe core, wherein one each of the sense coils being located in a respective one of the channels, wherein one each of the drive coils being co-located with the respective sense coil in a respective one of the channels, wherein the drive coils are connected in series, and wherein the sense coils are connected in anti-series.

In one embodiment, the drive coil is wound on top of the sense coil. In another embodiment, the regions of the probe core define two channels for containing coils of wire, one of the channels being adjacent the first end of the cylindrical probe core, wherein one each of the sense coils being located in a respective one of the channels, wherein one each of the drive coils being co-located with the respective sense coil in a respective one of the channels, wherein the drive coils are connected in anti-series, and wherein the sense coils are connected in series. In yet another embodiment, the regions of the probe define four channels for containing coils of wire, a respective two of the channels being located in each of the respective regions, wherein two of the channels are located adjacent the first end of the cylindrical probe core, wherein one each of the sense coils being located in a respective one of the channels in each one of the regions, wherein one each of the drive coils being located in a respective one of the channel in each one of the regions, wherein no two coils occupy the same channel, wherein the drive coils are connected in series, and wherein the sense coils are connected in anti-series.

In one embodiment, the regions of the probe define four channels for containing coils of wire, a respective two of the channels being located in each of the respective regions, wherein two of the channels are located adjacent the first end of the cylindrical probe core, wherein one each of the sense coils being located in a respective one of the channels in each one of the regions, wherein one each of the drive coils being located in a respective one of the channel in each one of the regions, wherein no two coils occupy the same channel, wherein the drive coils are connected in anti-series, and wherein the sense coils are connected in series. In another embodiment, the order of the coils from the first end toward the second end of the probe is sense coil, drive coil, sense coil, and drive coil. In still yet another embodiment, the order of the coils from the first end toward the second end of the probe is drive coil, sense coil, drive coil, and sense coil.

In one embodiment, the order of the coils from the first end toward the second end of the probe is sense coil, drive coil, drive coil, and sense coil. In yet another embodiment, the order of the coils from the first end toward the second end of the probe is drive coil, sense coil, sense coil, and drive coil. In still yet another embodiment, the sense coils and the drive coils have different diameters. In another embodiment, the sense coils and the drive coils have different numbers of turns.

In one embodiment, the probe further includes a third drive coil, the third drive coil in series connection between the first and the second drive coil and positioned between the first and second drive coil so as to form a single solenoidal drive coil, wherein one each of the sense coils being located near a respective end of the single solenoidal drive coil. In another embodiment, every turn of the single solenoidal drive coil is of the same diameter. In yet another embodiment, the longitudinal center turn of the single solenoidal drive coil has a greater diameter than turns on the ends of the solenoidal drive coil. In still another embodiment, every turn of the single solenoidal drive coil is of the same spacing. In still yet another embodiment, turns in the longitudinal center of the single solenoidal drive coil have a greater spacing than turns on the ends.

In one embodiment, the probe core comprises a material with a thermal diffusivity of substantially $\geq 20 \times 10^{-6}$ m$^2$/s and a thermal expansion coefficient of substantially $<3 \times 10^{-5}$/° C. In another embodiment, wherein the probe core comprises a material that has a thermal diffusivity of substantially $\geq 50 \times 10^{-6}$ m$^2$/s and a thermal expansion coefficient of substantially $<5 \times 10^{-6}$/° C.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

FIG. 6b is a graph of the field generated by the solenoidal coil of FIG. 6a;

DESCRIPTION OF AN EMBODIMENT OF THE INVENTION

Figure 1:
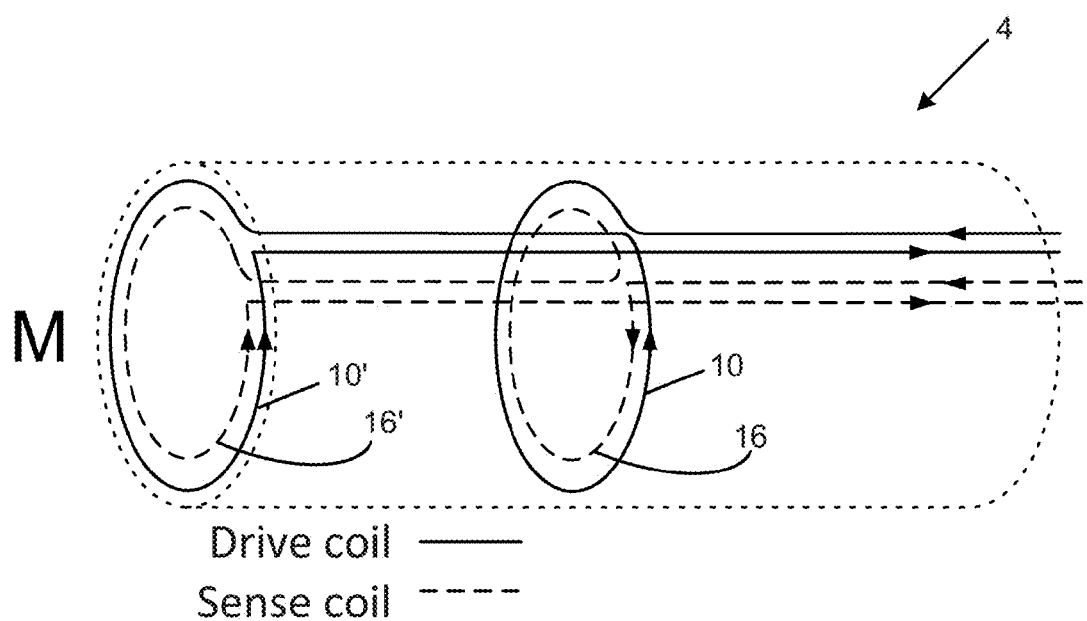
FIG. 1 is a block diagram of an embodiment of a probe constructed in accordance with the invention.

First, to improve the sensitivity of the coil while reducing its size, it is important to reduce any thermal effects on the operation of the probe, which is highly sensitive to relative change in geometry between the coils, particularly axial movement, and any change in the size of the coils. One of the thermal effects which must be addressed is any asymmetric expansion of the coil arrangement when the end of the probe comes into contact with a warm body, and the coil nearest to the body experiences a higher temperature than the coil further away. Reducing the temperature differential between the coils, while maintaining the low thermal expansion coefficient of the coil former or probe body, permits this sensitivity to be reduced. In other words, it is important to equalize any temperature differential across the coils rapidly so that a thermal gradient cannot be sustained by a thermal input at one end.

When a substance has high thermal diffusivity, heat moves rapidly through the substance because the substance conducts heat quickly relative to its volumetric heat capacity or "thermal bulk." Therefore, a material with high thermal diffusivity is desirable for the coil former (probe core material) in order to equalize the temperature across the coils as rapidly as possible. Further, suitable materials need to be non-magnetic, non-electrically conducting and have a relatively low thermal expansion coefficient. The low thermal expansion coefficient is required to reduce axial and radial expansion which affects the relative positions of the coils. Table 1 shows relevant properties of various materials.

In one embodiment, the material preferably has a thermal diffusivity of substantially $\geq 20 \times 10^{-6}$ m$^2$/s and a thermal expansion coefficient of substantially $<3 \times 10^{-5}$/° C. More preferably, the material has a thermal diffusivity of substantially $\geq 50 \times 10^{-6}$ m$^2$/s and a thermal expansion coefficient of substantially $<5 \times 10^{-6}$/° C. Such materials may include:

Glassy ceramics such as borosilicate based machinable ceramics e.g. Macor® (Corning Inc, New York);
  Non-glassy ceramics such as aluminum nitride, boron nitride, silicon carbide;
  Composite ceramics such as Shapal-M, a composite of boron nitride and aluminum nitride (Tokuyama Corporation, Shunan City, Japan); and
  Carbon- and glass-filled composites, for example glass or carbon filled Polyetheretherketone (PEEK).

Further, it is advantageous for the material to have a high stiffness to avoid change in the position of the coils due to mechanical deformation. In one embodiment, the material has a Young's Modulus of $\geq 40$ GPa and preferably $\geq 80$ GPa, and the material has as high a toughness as can be achieved given the other material constraints. For ceramics, in this application, the likely failure mode is energy- (or shock-) induced brittle fracture, for example when the probe is knocked or dropped. In this case, the relevant material property is the toughness $G_{ic} \approx K_{ic}^2/E$ (KJm$^{-2}$) which, along with other probe information, is tabulated in Table 2.

The probe's sensitivity to temperature changes is further reduced by minimizing heat transfer into the probe from outside of the probe. This is achieved by using a high conductivity polymer material for the case, so that the inside surface of the case is closer to an isothermal surface, thus minimizing thermal gradients inside the probe and providing an insulating layer of air or a highly insulating material such as aerogel or a vacuum gap around the probe core, or former, and windings. In addition to the selection of materials, the coil configurations may be selected to reduce thermal effects.

In one embodiment, the probe includes a coil former with two sense coils and two drive coils. The sense and drive coils are arranged in two pairs, each consisting of one sense coil and one drive coil in close proximity to one another. The probe's magnetic sensing performance is maximized by locating one sense and drive coil pair close to the sensing tip of the probe, and locating the second pair of coils an axial distance away from the first pair of coils. The distance is preferably greater than the diameter of the smallest coil, and more preferably greater than the diameter of the largest coil in the pair. By way of example, in one embodiment, the diameter of the largest coil is 15 mm, and in another embodiment, the diameter is 12 mm. In addition, each pair of coils is arranged such that the voltage induced in each of the sense coils by the field generated by the drive coils is approximately equal and opposite. For example, if there are two sense/drive coil pairs S1, D1 and S2, D2, separated by at least a coil diameter, the current induced in S1 by the combined drive fields from D1 and D2 is equal and opposite to the current induced in S2 by the combined drive fields from D1 and D2. Preferably, the sense coils are arranged as a first order gradiometer in order to minimize the effect of far field sources.

In one embodiment of the probe 4 (FIG. 1), the coils 10, 10', 16, 16' are co-located such that each drive coil 10, 10' is co-located with a sense coil 16, 16'. Either order of the arrangement of the sense and drive coils can be used. In one embodiment, the drive coil is wound on top of the sense coil in order to minimize any effect from thermal expansion of the drive coils as the drive coils warm due to ohmic heating. This arrangement is useful where thermal effects are less important than sensitivity at very small diameters (e.g. <15 mm). Because this arrangement does not require specific diameters and spacing of the drive and sense coils, it is suitable for use in probes of a very small outer diameter. In one embodiment, this probe has a diameter of less than 15 mm or even less than 10 mm in diameter.

Figure 2:
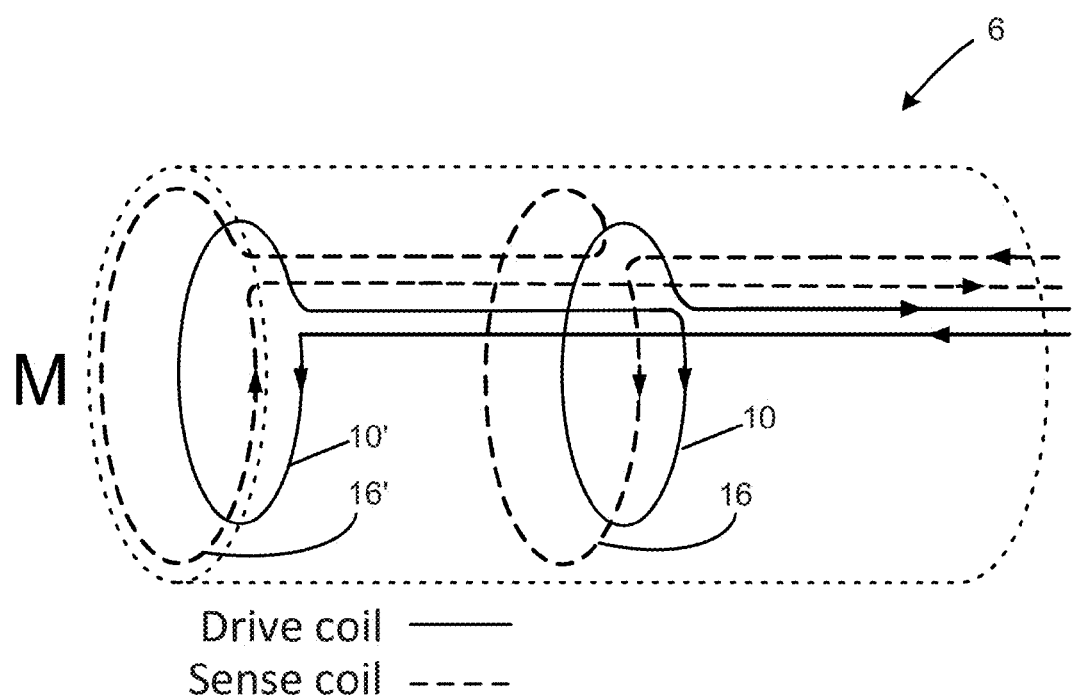
FIG. 2 is a block diagram of another embodiment of a probe constructed in accordance with the invention.
Figure 3:
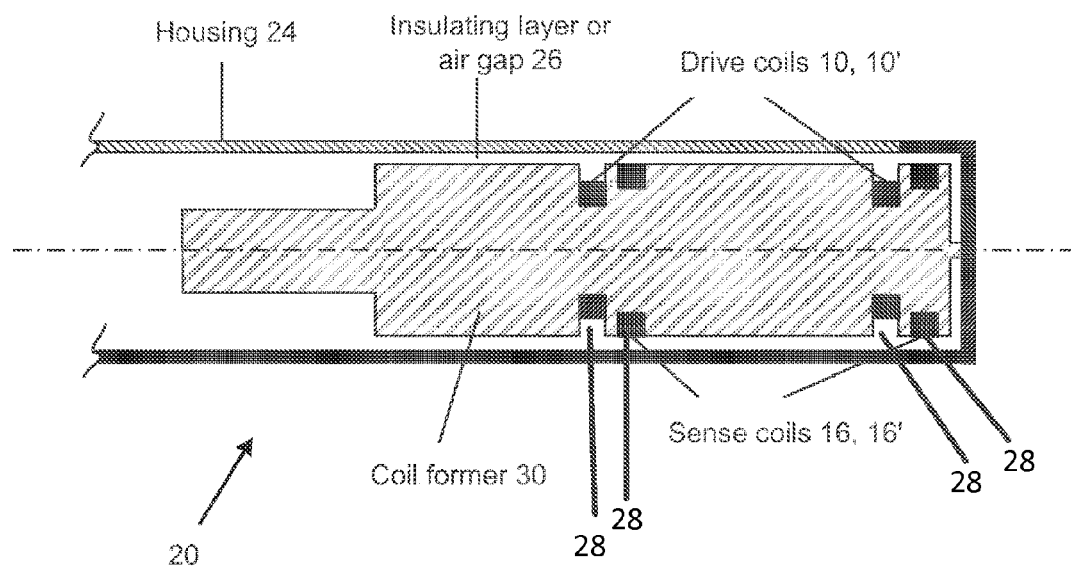
FIG. 3 is a cross-sectional diagram of the embodiment of the probe of FIG. 2.

In another embodiment of the probe 6 (FIG. 2), drive 10, 10' and sense 16, 16' coils are staggered with the drive coils 10, 10' being separated and the sense coils 16, 16' are divided into two parts. The spacing of the drive coil relative to the sense coil in each pair is chosen such that the effects of the expansion of the larger of the two coils on the mutual inductance of the pair of coils is minimized. This helps further to minimize the effect of thermal expansion. This arrangement provides improved sensing because the sensitivity drops off more slowly with distance. In this arrangement, the sense coil is closest to the sensing end of the probe in order to maximize sensing distance. In this arrangement, from the sensing end, the coil order is SD-SD where D represents a drive coil and S represents a sense coil. Referring to FIG. 3, a cross-section of an embodiment of a probe 20 is shown including a housing 24, temperature barrier 26 and a coil former or probe core 30 having circumferential grooves 28 into which the coils 10, 10', 16. 16' are formed.

Other embodiments which maintain the relative arrangement of each drive/sense pair also fall within the scope of the invention. These embodiments include different orders and symmetry of the pairs, e.g. SD-DS, DS-DS and DS-SD, as well as varying spacing between the pairs of coils. In each case, the coils are connected such that one of the drive pair of coils or the sense pair of coils forms a gradiometer. The other pair of sense coils or drive coils is wired in series, i.e. with the same sense to form a simple magnetometer. A higher order gradiometer can be used for either set of coils, providing that in each case the order of gradiometer of the drive set of coils differs by one from the order of gradiometer of the sense set of coils. For example, the sense coils may form a second order gradiometer and the drive coils may form a first (or third) order gradiometer.

In one embodiment, the winding is arranged together with the electronic circuit such that the outside layer of the coil winding is close to ground potential of the electronics. This minimizes the capacitive coupling between the probe and the patient's body which is assumed to be at ground potential.

Further embodiments include making the sense coil the larger of the two diameters (rather than the drive coil) in combination with any of the above. If a smaller gauge wire is used for the sense coil (as it carries only a tiny current), then making the sense coil the larger of the two is advantageous because it allows the average diameters of the drive and sense coils to be maximized within the specific arrangement of the sense coil/drive coil pairs. Increasing the diameter and therefore the areas of the coils increases the sensitivity of the magnetic sensor. A larger gauge of wire may be used for the drive coil in order to minimize ohmic heating.

Further, when the diameter of the probe is reduced, the magnetic sensitivity is commensurately reduced by a factor of $r^4$ in the near field (drive field drops off with $r^2$ and sensing capability with $r^2$) and $r^6$ in the far field. Therefore, in order to maintain a similar level of magnetic sensitivity in a smaller diameter probe, the number of turns in the coils, particularly in the sense coils, is increased. However, as a side effect, this also magnifies any noise or drift by the same factor. Thus, drift due to changes in the coil geometry caused by temperature changes should be expected to be magnified.

However, by using the staggered coil arrangement and the Shapal-M coil core, the thermal drift due to warm body contact can be maintained at an acceptable level. For example, with a smaller diameter probe of the staggered coil arrangement, the signal change in response to contact with a warm body at 37° C. is about 86% of the equivalent signal change in one of the prior art systems. Because the smaller probe has twice as many coil turns, the signal change should therefore be much greater than this.

Figure 4:
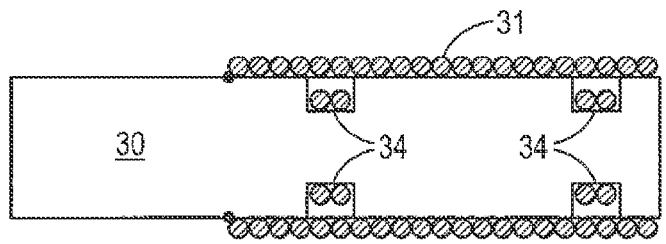
FIG. 4 is a block diagram of another embodiment of a probe using a solenoid coil constructed in accordance with the invention.

In a further embodiment (FIG. 4), a solenoid 31 is used as the excitation (drive) coil and two sense coils 34 are positioned inside the solenoid 31. As long as the sense coils 34 are not too close to the end of the solenoid 31, they will experience a substantially uniform magnetic field from the solenoid 31. The benefit of this arrangement is that small movements relative to the solenoid 31, for example due to thermal expansion, will not disturb the (magnetic) balance of the sense coils 34. Further, the solenoid will also provide an additional heat conduction path to the sense coils and the coil core to help equalize temperature across all the coils. By choosing the wire gauge, the ohmic heating effect of the solenoid can be minimized. The solenoid coil also forms an electrostatic shield for the sense coil.

Figure 5:
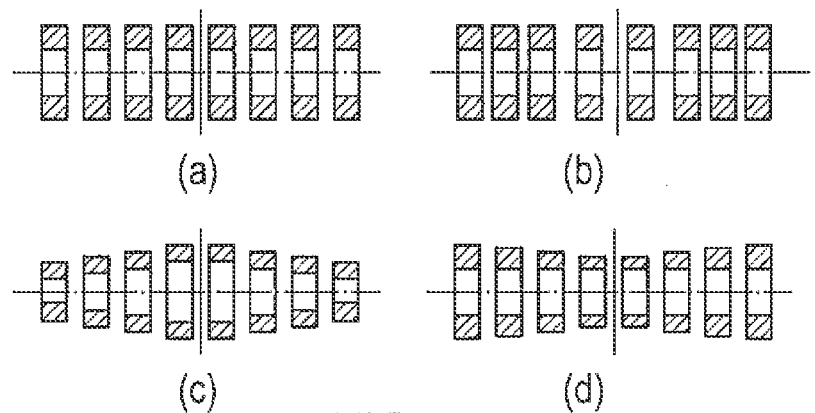
FIG. 5 (a-d) are cross-sections of four solenoid coil configurations.

The more uniform the field is close to the ends of the solenoid, the closer the sense coils can be positioned to the end of the probe, and the better the sensitivity. The uniformity of the field at the ends of the solenoid is optimized by appropriate design of the coils, for example, by varying the spacing, the diameter, both the spacing and diameter, or the shape of the solenoid coils (FIG. 5 (a-d)). Design and manufacturing of such solenoids is known to those skilled in the art.

Figure 6A:
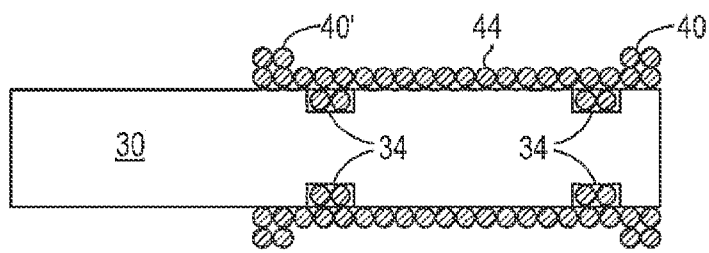
FIG. 6a is a cross section of a solenoidal coil with additional coils on each end.
Figure 6B:
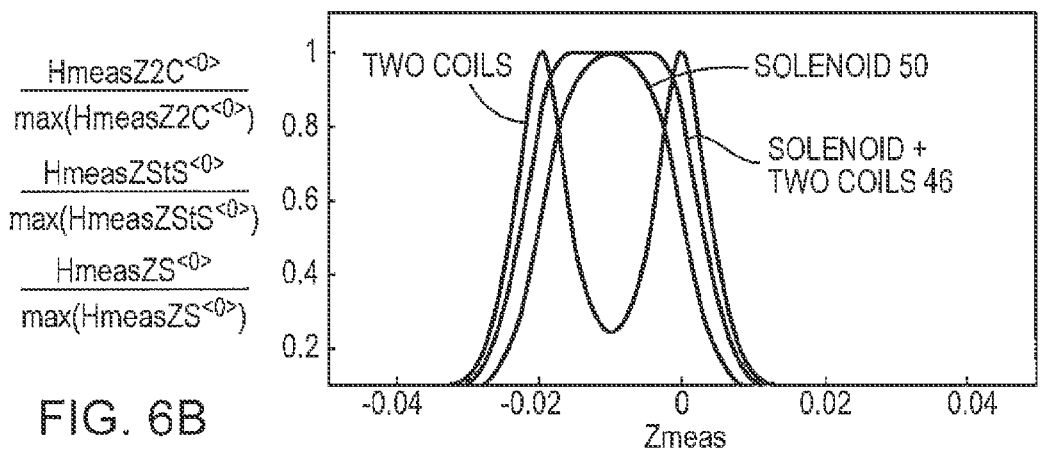
Figure 7:
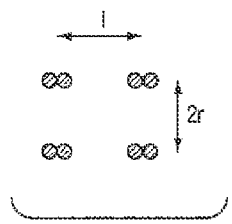
FIG. 7 is a cross-sectional representation of a Helmholtz coil embodiment.

A particular example is shown in FIG. 6a, together with a graph (FIG. 6b), showing the results of modeling the resulting normalized magnetic field strength. By adding two coils 40, 40' at the end of the solenoid 44, the field uniformity along the length can be improved (46) over the field of the solenoid alone (50). A special case of the solenoid drive coil is one in which the drive coil is formed from a Helmholtz pair of coils where the separation between the coils, l, is substantially equal to the radius of the coils (r) (FIG. 7). The Helmholtz coil is a well-known arrangement that provides a region of constant magnetic field between the two coils, and this region extends further than in any other arrangement of the coils with a different ratio of separation-to-radius.

Figure 8:
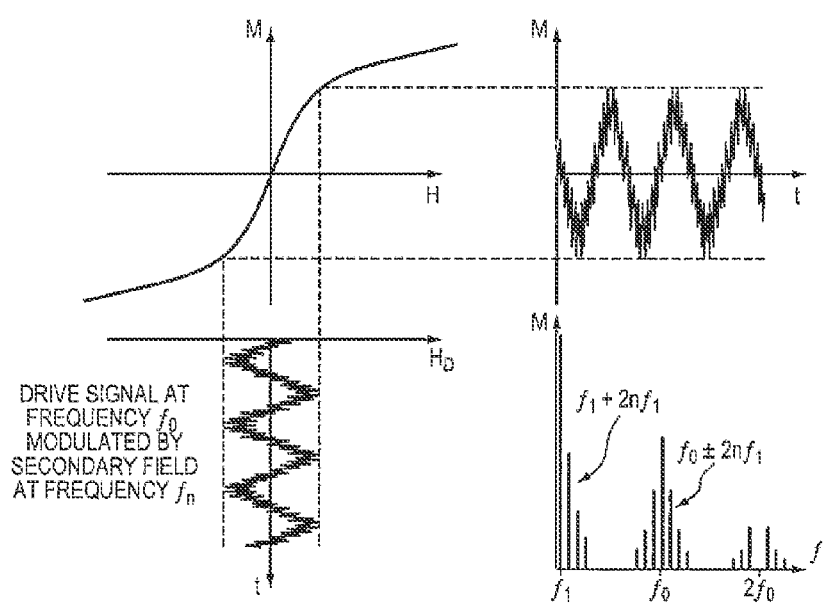
FIG. 8 is a graph of the modulation of a primary magnetic field with a secondary magnetic field and the resulting frequency spectrum.

In addition to manipulating the coils and their structure and locations, a further embodiment addresses the issue of distinguishing between the signal from the iron oxide nanoparticles and the signals from other metallic objects. In this embodiment, a second varying magnetic drive field is generated at a lower frequency than the primary drive field and with comparable or greater magnitude than the primary drive field. The secondary drive field modulates the susceptibility of the magnetic nanoparticles and creates additional frequency components in the spectrum received by the sense coils at frequencies $f_0 \pm 2nf_1$, where $f_0$ is the primary drive field frequency and $f_1$ is the secondary drive field frequency and n is a whole number (FIG. 8). The presence of magnetic nanoparticles can be detected by analyzing these additional frequencies that are a result of the mixing of the primary and secondary drive frequencies.

In one embodiment, the amplitude of the side lobe at $f_0 \pm 2f_1$ is measured to detect the presence of magnetic nanoparticles. In an alternative embodiment, the ratio of the amplitude $A_{f0 \pm 2f1}$ of the side lobe to the amplitude $A_{f0}$ of the fundamental ($A_{f0 \pm 2f1}/A_{f0}$) is measured. Other embodiments are possible that result in an advantageous combination of frequencies. These components are less sensitive or even insensitive to coil structure and geometric imbalance, temperature effects, and also to eddy currents. Thus, by appropriate signal processing, the undesirable disturbance from coil structure and geometric imbalance, temperature sensitivity, and metallic objects can be reduced or eliminated.

In practice, the geometrical symmetry of construction needed for a perfect electromagnetic balance is very difficult to achieve within the constraints of state-of-the-art and cost-effective construction, and there is usually some level of residual imbalance. Furthermore, temperature fluctuations experienced by the coils, particularly non-uniform changes, for example when the end of the probe (near one coil) comes into contact with a warm body, will create additional dynamic imbalance in the coils as the geometry of the coils varies slightly due to thermal expansion.

These imbalances in the coils manifest themselves as a disturbance signal at the fundamental primary drive frequency $f_0$, caused by the sense coil detecting a non-cancelled residual direct magnetic signal from the drive coils. However, any signal at a mixed or modulated frequency $f_0 \pm 2nf_1$ resulting from the secondary frequency $f_1$ is only generated by the magnetic response of the nanoparticles to $f_1$, and therefore at these frequencies there is no disturbance signal component caused by any coil imbalance. Thus, by extracting these components from the overall signal received by the sense coils, these frequency components can be used to detect the presence of the nanoparticles and distinguish them from disturbance caused by magnetic imbalance of the coils whether caused by imperfections in construction or thermally-induced distortions.

Further, the drive field from the probe will induce eddy currents in any electrically conducting object, e.g. metallic surface that is sufficiently close, and the magnetic field created by the eddy currents may then be picked up by the sense coils as an extraneous signal. However, as with the imbalances described above, there is no frequency mixing with the signals produced by eddy currents. Thus, the mixed or modulated frequencies $f_0 \pm 2nf_1$ do not show any component of fields generated by eddy currents, which means that non-ferromagnetic materials can be distinguished from nanoparticles. Thus, by extracting these components from the overall signal received by the sense coils, these $f_1$ frequency components can be used to detect the presence of the nanoparticles and distinguish them from non-ferromagnetic materials. Because the nanoparticles generate side lobes, the existence of side lobes are indicative of nanoparticles and one such measure of the presence of nanoparticles is obtained by measuring the amplitude of the side lobe. The greater the side lobe amplitude, the more nanoparticles are being determined. To adjust for noise in the signals, it is possible to normalize the measurement of the presence of nanoparticles by using the ratio of the amplitude $A_{f_0 \pm 2nf_1}$ of a side lobe to the amplitude $A_{f_0}$ of the fundamental ($A_{f_0 \pm 2nf_1}/A_{f_0}$) where n is a whole number.

An additional benefit of making the system insensitive to eddy currents is that the primary drive frequency can be increased to take advantage of the increased sensitivity of the magnetic nanoparticles at higher frequencies. For example, the frequency could be increased to significantly more than 10 kHz; e.g., to 50 kHz or 100 kHz or 250 kHz or more. However, ferromagnetic materials will exhibit both eddy current and magnetic responses, and have similar non-linear magnetic properties to the nanoparticles. Hence, the magnetic part of the response is not readily distinguishable from the magnetic nanoparticles.

Because the magnetic nanoparticles have a non-linear frequency response, the response of the particles can be distinguished from the diamagnetic effect of the body, which has a linear effect. Therefore, the present invention can also be used to screen out the diamagnetic effect.

The use of a secondary drive field is suitable for use with any of the coil embodiments and, for any given embodiment, the detection of the magnetic field will be much less sensitive to imbalances in the coils. This system does not require a balanced coil arrangement, provided that the fundamental frequency can be filtered out effectively, although practically this may be desirable for other reasons, e.g. to avoid saturating the input electronics.

The frequency of the secondary drive field is chosen to provide sufficient frequency separation from the primary drive frequency band. This may be, for example, in the region of 0.5% to 10% of the primary frequency and preferably in the range of 1% to 5%. For a primary frequency of 100 kHz, a secondary frequency of 10 Hz to 10 kHz, and more preferably between 100 Hz and 1 kHz, could be used. For example, in one embodiment the primary frequency is 100 kHz and the secondary 1 kHz. Advantageously, the secondary frequency may be chosen to be a multiple of the power supply frequency, e.g. n×50 or n×60 Hz, such that the secondary drive can be derived from power supply frequency, but the power supply frequency does not interfere with the sensing. For example, the primary frequency may be 10 kHz and the secondary frequency 200 Hz. Further, a resonant drive circuit may be used for generating the primary field to maximize the magnetic field strength for a given level of power input. For clinical applications like sentinel lymph node biopsy, a secondary field strength in the region of interest of at least 15 microTesla, and preferably greater than 25 microTesla, is appropriate.

In one embodiment, the secondary field is generated by the handheld probe containing the sensing and primary drive fields, for example by having a moving permanent magnet. The movement of the magnet can be, for example, an oscillatory, rotating or vibratory movement. Alternatively, in one embodiment, an additional coil is added to the probe and is driven so as to create a time varying magnetic field. In another embodiment, the secondary field is generated away from the probe, for example by means of a device placed near the patient. In another embodiment, the field is generated in a pad that sits underneath the area of the patient that is being sensed. In this case, a coil diameter of at least 200 mm is desirable and a field strength of 2.5 mT (or H field of 2000 A/m) is desirable at the center of the coil to provide sufficient secondary field strength in the region of interest where the probe will be used.

Figure 9:
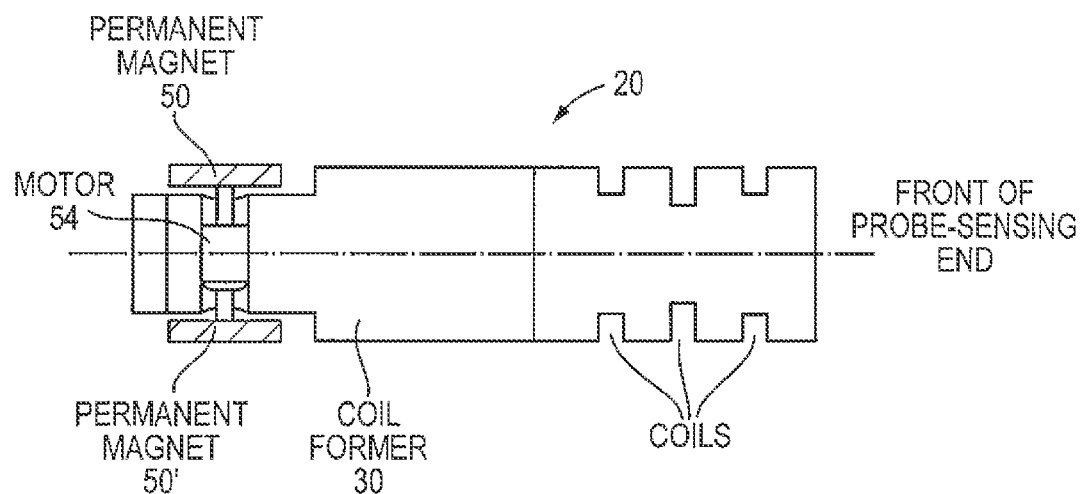
FIG. 9 is an embodiment of a secondary field generator for use in creating the secondary magnetic field shown in FIG. 8.
Figure 10:
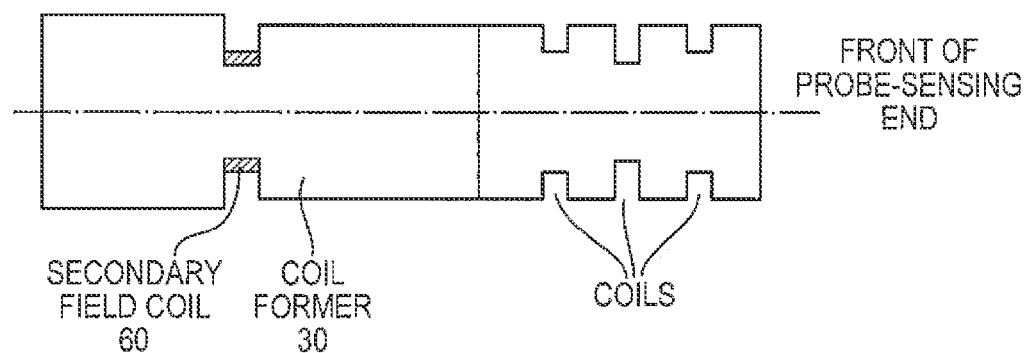
FIG. 10 is an embodiment of a secondary field generator for use in creating the secondary magnetic field shown in FIG. 8.

In more detail, and referring to FIG. 9, an alternating secondary field can be generated by rotating a permanent magnet 50, 50' using a motor 54 rotating at the desired frequency. The rotating permanent magnet has the advantage that it is contained within the handheld probe. Such a small motor 54 is capable of spinning a rare earth magnet 50 such that the magnetic polarity of the magnet changes with each rotation. Alternatively, and referring to FIG. 10, the secondary field may be generated electromagnetically by a drive coil 60 located at the rear of the handheld probe driven by a signal generator.

It should be understood that the order of steps or order for performing certain actions is immaterial so long as the present teachings remain operable. Moreover, two or more steps or actions may be conducted simultaneously.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A handheld magnetic susceptometry probe for detecting a magnetic marker within a body comprising: a probe core having a first end and a second end, the probe core defining two longitudinal regions for containing coils of wire, one of the regions being adjacent the first end of the cylindrical probe core; two sense coils, one each of the sense coils being located in a respective one of the regions; and two drive coils, one each of the drive coils being located in a respective one of the regions, wherein the regions are longitudinally separated by a distance equal to or greater than the diameter of one of the coils, wherein the drive coil and the sense coil in each region are in close proximity.

2. The probe of claim 1 wherein the magnetic marker comprises magnetic nanoparticles.

3. The probe of claim 1 wherein one of the set of two drive coils and the set of two sense coils is connected as a gradiometer, and the other of the set of two drive coils and the set of two sense coils is connected in series.

4. The probe of claim 3 wherein the sense coils and the drive coils have different diameters, and the diameter of the sense coils is greater than the diameter of the drive coils.

5. The probe of claim 4 wherein the sense coils and the drive coils have different diameters the diameter of the largest coil is less than 15 mm.

6. The probe of claim 4 wherein the wire of the drive coils have different numbers of turns has a larger gauge than the wire of the sense coils.

7. The probe of claim 4 wherein the sense coils and the drive coils have different numbers of turns.

8. The probe of claim 1:
wherein the regions of the probe core define two channels for containing coils of wire, one of the channels being adjacent the first end of the cylindrical probe core,
wherein one each of the sense coils being located in a respective one of the channels,
wherein one each of the drive coils being co-located with the respective sense coil in a respective one of the channels,
wherein the drive coils are connected in series, and
wherein the sense coils are connected in anti-series.

9. The probe of claim 1 wherein the drive coil is wound on top of the sense coil.

10. The probe of claim 1:
wherein the regions of the probe core define two channels for containing coils of wire, one of the channels being adjacent the first end of the cylindrical probe core,
wherein one each of the sense coils being located in a respective one of the channels,
wherein one each of the drive coils being co-located with the respective sense coil in a respective one of the channels,
wherein the drive coils are connected in anti-series, and
wherein the sense coils are connected in series.

11. The probe of claim 1 further comprising:
a third drive coil, the third drive coil in series connection between the first and the second drive coil and positioned between the first and second drive coil so as to form a single solenoidal drive coil,
wherein one each of the sense coils being located near a respective end of the single solenoidal drive coil.

12. The probe of claim 11 wherein every turn of the single solenoidal drive coil is of the same diameter.

13. The probe of claim 11 wherein turns in the longitudinal center of the single solenoidal drive coil have a greater diameter than turns on the ends.

14. The probe of claim 11 wherein every turn of the single solenoidal drive coil is of the same spacing.

15. The probe of claim 11 wherein turns in the longitudinal center of the single solenoidal drive coil have a greater spacing than turns on the ends.

16. The probe of claim 1 wherein the probe core comprises a material with a thermal diffusivity of substantially $\geq 20 \times 10^{-6}$ m$^2$/s wherein thermal diffusivity is defined as (Thermal conductivity/{Density×Specific heat capacity}).

17. The probe of claim 1 wherein the probe core comprises a material with a toughness $G_{ic}$ of greater than $9 \times 10^{-3}$ KJm$^{-2}$, wherein toughness is defined as {Fracture toughness, $K_{ic}$}$^2$/ Young's Modulus.

18. The probe of claim 17 wherein the probe core comprises a ceramic selected from the group consisting of boron nitride, aluminium nitride, silicon carbide, Shapal-M, Macor and combinations thereof.

* * * * *